United States Patent
Gray et al.

(10) Patent No.: US 10,807,868 B2
(45) Date of Patent: Oct. 20, 2020

(54) CATALYSTS AND RELATED METHODS FOR PHOTOCATALYTIC PRODUCTION OF $H_2O_2$ AND THERMOCATALYTIC REACTANT OXIDATION

(71) Applicant: NORTHWESTERN UNIVERSITY, Evanston, IL (US)

(72) Inventors: Kimberly A. Gray, Evanston, IL (US); Justin M. Notestein, Evanston, IL (US); Todd R. Eaton, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/680,675

(22) Filed: Nov. 12, 2019

(65) Prior Publication Data
US 2020/0095126 A1 Mar. 26, 2020

Related U.S. Application Data

(62) Division of application No. 15/073,892, filed on Mar. 18, 2016, now Pat. No. 10,508,032.

(Continued)

(51) Int. Cl.
*C07D 301/12* (2006.01)
*C01B 15/026* (2006.01)
(Continued)

(52) U.S. Cl.
CPC .............. *C01B 15/026* (2013.01); *B01J 21/08* (2013.01); *B01J 23/06* (2013.01); *B01J 23/14* (2013.01); *B01J 23/20* (2013.01); *B01J 23/22* (2013.01); *B01J 23/26* (2013.01); *B01J 23/28* (2013.01); *B01J 23/30* (2013.01); *B01J 23/34* (2013.01); *B01J 23/36* (2013.01); *B01J 23/466* (2013.01); *B01J 23/468* (2013.01); *B01J 23/72* (2013.01); *B01J 23/75* (2013.01); *B01J 27/22* (2013.01); *B01J 35/002* (2013.01); *B01J 35/004* (2013.01); *B01J 35/0006* (2013.01); *B01J 35/008* (2013.01); *B01J 35/0086* (2013.01);
(Continued)

(58) Field of Classification Search
CPC . B01J 21/08; B01J 35/004; B01J 23/14; B01J 23/466; B01J 23/26; B01J 23/06; B01J 23/08; B01J 23/36; B01J 23/30; B01J 23/75; B01J 23/22; B01J 23/34; B01J 23/468; B01J 23/72; B01J 23/20; B01J 37/0209; B01J 37/06; B01J 37/08; B01J 35/002; B01J 35/0006; B01J 35/0086; B01J 35/008; B01J 35/1057; C01B 15/026; C07D 301/12; C07C 29/145
USPC ......................................................... 549/531
See application file for complete search history.

(56) References Cited

U.S. PATENT DOCUMENTS 5,262,550 A * 11/1993 Crocco .................... B01J 29/89
549/531
5,756,778 A * 5/1998 Thiele ...................... B01J 29/80
549/531

OTHER PUBLICATIONS

Shiraishi et al, Selective Hydrogen Peroxide Formation by Titanium Dioxide Photocatalysis with Benzylic Alcohols and Molecular Oxygen in Water, ACS Catal. 2013, 3, 2222-2227) (Year: 2013).*

* cited by examiner

*Primary Examiner* — Taylor V Oh
(74) *Attorney, Agent, or Firm* — Bell & Manning, LLC

(57) ABSTRACT

Catalysts, catalytic systems and related synthetic methods for in situ production of $H_2O_2$ and use thereof in reaction with oxidizable substrates.

14 Claims, 8 Drawing Sheets

Related U.S. Application Data

Figure 1:
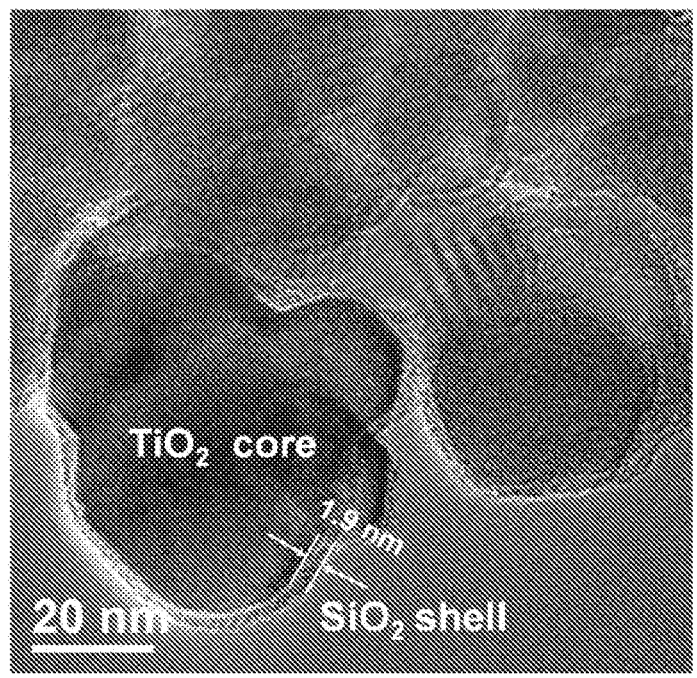

(60) Provisional application No. 62/136,073, filed on Mar. 20, 2015.

(51) Int. Cl.
| | |
|---|---|
| *C07C 29/145* | (2006.01) |
| *B01J 21/08* | (2006.01) |
| *B01J 35/00* | (2006.01) |
| *B01J 23/14* | (2006.01) |
| *B01J 23/46* | (2006.01) |
| *B01J 37/02* | (2006.01) |
| *B01J 37/06* | (2006.01) |
| *B01J 23/26* | (2006.01) |
| *B01J 23/06* | (2006.01) |
| *B01J 23/28* | (2006.01) |
| *B01J 27/22* | (2006.01) |
| *B01J 37/08* | (2006.01) |
| *B01J 23/36* | (2006.01) |
| *B01J 23/30* | (2006.01) |
| *B01J 23/75* | (2006.01) |
| *B01J 23/22* | (2006.01) |
| *B01J 23/34* | (2006.01) |
| *B01J 37/34* | (2006.01) |
| *B01J 35/10* | (2006.01) |
| *B01J 23/72* | (2006.01) |
| *B01J 23/20* | (2006.01) |

(52) U.S. Cl.
CPC ....... *B01J 35/1057* (2013.01); *B01J 37/0209* (2013.01); *B01J 37/06* (2013.01); *B01J 37/08* (2013.01); *B01J 37/34* (2013.01); *C07C 29/145* (2013.01); *C07D 301/12* (2013.01)

CATALYSTS AND RELATED METHODS FOR PHOTOCATALYTIC PRODUCTION OF $H_2O_2$ AND THERMOCATALYTIC REACTANT OXIDATION

The present application is a divisional of U.S. patent application Ser. No. 15/073,892 filed Mar. 18, 2016, the entire contents of which are hereby incorporated herein by reference; which claims priority to U.S. provisional patent application No. 62/136,073, filed on Mar. 20, 2015, the entire contents of which are hereby incorporated herein by reference.

This invention was made with government support under DE-SC0006718 awarded by the Department of Energy. The government has certain rights in the invention.

BACKGROUND OF THE INVENTION

Approximately 3.5 million metric tons of hydrogen peroxide ($H_2O_2$) are produced globally each year for use in waste treatment, pulp and paper bleaching, and the chemical industry. $H_2O_2$ is an environmentally-friendly, atom-efficient, and selective oxidant for chemical synthesis. Unfortunately, current industrial-scale synthesis is problematic. Direct synthesis from $H_2$ and $O_2$ has been largely unsuccessful and is inherently dangerous. $H_2O_2$ is environmentally unfriendly, expensive, and difficult to carry out at all but the largest scale. Moreover, $H_2O_2$ must be diluted before shipping.

Accordingly, there remains an ongoing effort in the art to develop a safe, efficient and economical method for $H_2O_2$ production, to utilize the benefits and advantages associated with this oxidant.

SUMMARY OF THE INVENTION

In light of the foregoing, it is an object of the present invention to provide catalyst material(s) and related method(s) for the production of $H_2O_2$ and use in selective oxidation reactions, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide in situ $H_2O_2$ production without dilution and transportation safety issues associated with the prior art.

It can also be an object of the present invention to provide a catalyst material whereby photocatalytic properties, for $H_2O_2$ production, and thermocatalytic properties, for substrate oxidation, can be independently tuned and optimized.

It can also be an object of the present invention, alone or in conjunction with one or more of the preceding objectives, to provide photo- and thermocatalytic functions with a single catalyst material.

Other objects, features, benefits and advantages of the present invention will be apparent from this summary and the following descriptions of various preferred embodiments, and will be readily apparent to those skilled in the art having knowledge of various $H_2O_2$ production and related oxidation techniques. Such objects, features, benefits and advantages will be apparent from the above as taken into conjunction with the accompanying examples, data, figures and all reasonable inferences to be drawn therefrom.

The present invention can be directed to a catalytic system comprising a photocatalyst for production of $H_2O_2$ from $O_2$ and a proton donor component, such a photocatalyst comprising a particulate $TiO_2$ core component and a $SiO_2$ shell component coupled to such a core component, such a photocatalyst comprising $TiO_2$ surface areas; a thermocatalyst for reactant oxidation with produced $H_2O_2$, such a thermocatalyst adjacent to such a photocatalyst and comprising a $SiO_2$ component and a transition metal moiety coupled thereto; a reaction medium comprising $O_2$, a proton donor component and an oxidizable reactant component; and ultra-violet radiation introduced to such a reaction medium for a time and at a wavelength sufficient to produce $H_2O_2$ and oxidize such a reactant component therewith.

In certain embodiments, a proton donor component of such a system can be selected from methanol, ethanol, propanols, butanols, ethylene glycol, propylene glycol, glycerol, and carbohydrates. Regardless, such an oxidizable reactant component can be selected from alkenes, including but not limited to styrene and other styrenic compounds, cycloalkenes, allyl chloride, allyl alcohol and related such unsaturated reactants. Without limitation, a transition metal moiety of such a system can be selected from V, Ti, Cr, Mn, Co, Cu, Zn, Mo, Nb, Ta, W, Os, Re, Ir, and Sn moieties. In certain embodiments, such a transition metal moiety can be Ti. In certain such embodiments, such an alkene reactant component can be propylene.

Such a catalytic system can comprise both a photocatalyst and a thermocatalyst provided on such a $TiO_2$ core component, with such a transition metal moiety coupled to such $SiO_2$ shell component. In certain embodiments, such a transition metal can be Ti, and such an oxidizable reactant component can be propylene. Regardless, such a system can further comprise a catalyst to regenerate a proton donor component. For instance and without limitation, where such a proton donor source is isopropanol and a by-product of $H_2O_2$ production is acetone, such a system can comprise a hydrogenation catalyst to reduce acetone and regenerate isopropanol.

In part, the present invention can also be directed to a composition comprising a nanoparticulate $TiO_2$ core component; a $SiO_2$ shell component coupled to such a core component; and a transition metal moiety coupled to such a shell component, such a composition comprising pores comprising $TiO_2$ surface areas. In certain embodiments, such a transition metal moiety can be selected from V, Ti, Cr, Mn, Co, Cu, Zn, Mo, Nb, Ta, W, Os, Re, Ir, and Sn moieties. Regardless, such a shell component can have a thickness dimension of about 1.5-about 3.5 nm.

In part, the present invention can also be directed to a method for concomitant $H_2O_2$ production and reaction. Such a method can comprise providing a reaction medium comprising a catalyst composition of the sort discussed above or illustrated elsewhere herein, a proton donor component for photoreduction of $O_2$, and an oxidizable reactant component; introducing $O_2$ to such a reaction medium; and irradiating such an oxygenated reaction medium with ultra-violet light of a wavelength and for a time sufficient to produce $H_2O_2$ and oxidize such a reactant component within such a reaction medium. In certain embodiments, such a proton donor component can be selected from alcohols. In certain other embodiments, without regard to proton donor component, such an oxidizable reactant component can, as discussed above, be selected from various alkenes. As a separate consideration, such a transition metal moiety can be selected from V, Ti, Cr, Mn, Co, Cu, Zn, Mo, Nb, Ta, W, Os, Re, Ir, and Sn moieties. Without limitation, such an alkene can be propylene, and such a method can comprise oxidation thereof to propylene oxide. Regardless, as discussed above and illustrated elsewhere herein, such a method can comprise regeneration of such a proton donor source.

In part, the present invention can also be directed to a method of using a single catalyst for hydrogen peroxide production and alkene oxidation. Such a method can comprise providing a reaction medium comprising a single catalyst composition comprising a nanoparticulate $TiO_2$ core component, a $SiO_2$ shell component coupled to such a core component and a transition metal moiety coupled to such a shell component, a proton donor component and an alkene component, such a composition comprising a photocatalytic $TiO_2$—$SiO_2$ component and a thermocatalytic transition metal-$SiO_2$ component and pores comprising $TiO_2$ surface areas; introducing $O_2$ to such a reaction medium; and irradiating such an oxygenated reaction medium with ultraviolet light of a wavelength and for a time sufficient to produce hydrogen peroxide and oxidize such an alkene component within such a reaction medium. Proton donor components and transition metals can be selected from those discussed above or illustrated elsewhere herein. Without limitation, such an alkene component can be selected from cyclo- and straight-chain alkenes. In certain such embodiments, such an alkene can be propylene, which can be oxidized to propylene oxide.

DETAIL DESCRIPTION OF THE DRAWINGS

FIG. 1: TEM image of $SiO_2$@$TiO_2$ core-shell material, in accordance with certain non-limiting embodiments of this invention.

Figure 2:
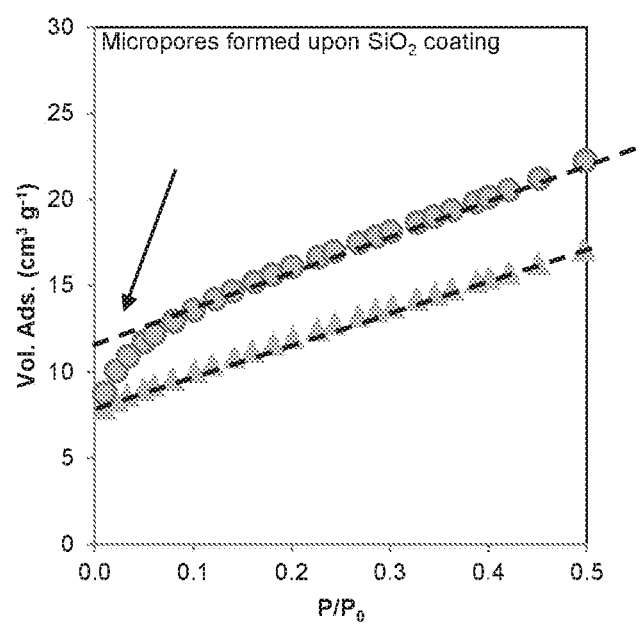

FIG. 2: $N_2$ adsorption isotherms for $TiO_2$ core (▲) and $SiO_2$@$TiO_2$ (●) materials. In the region below $P/P_0$=0.06 there is less than monolayer coverage for the core-shell material, indicating the presence of microporosity. This adsorption phenomenon is absent for the $TiO_2$ core material.

Figure 3:
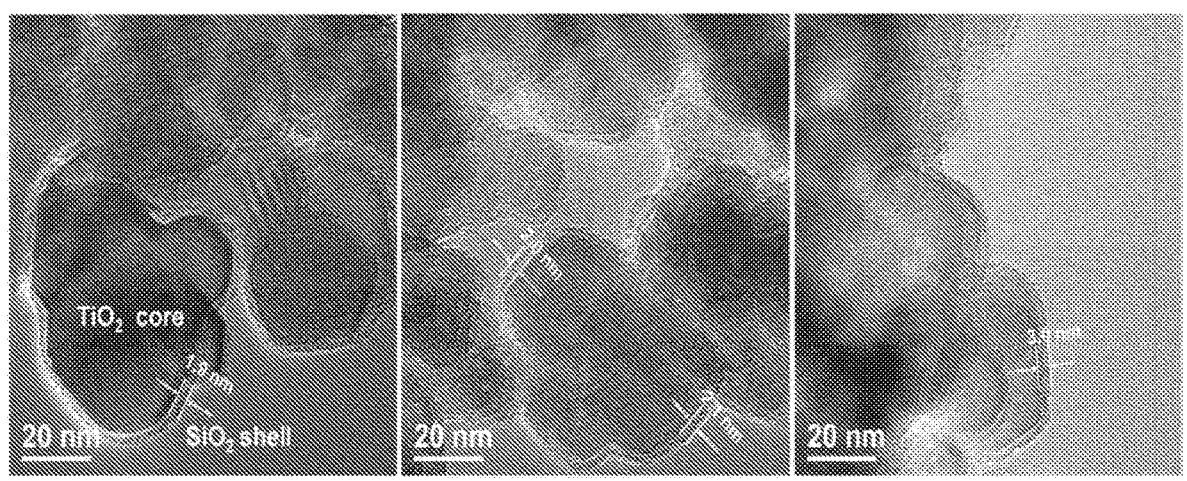

FIG. 3: TEM images of the $SiO_2$@$TiO_2$ material with silica shell thickness between 1.9 and 3.0 nm.

Figure 4:
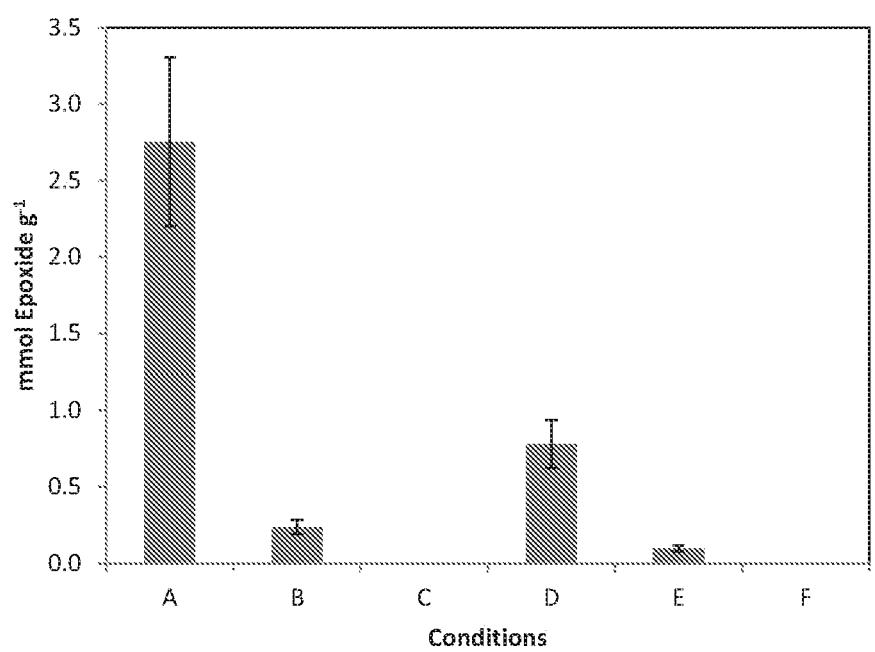

FIG. 4: Epoxide yields after 2 hours for control reactions for the combined photo-/thermo-catalytic system and Ti—$SiO_2$@$TiO_2$ catalyst: (A) standard conditions (isopropanol, $O_2$, UV light and 65° C.), (B) standard conditions except at room temperature, (C) standard conditions except no UV illumination, (D) standard conditions except using dodecane as solvent (i.e., less effective proton donor and hole scavenger than IPA for $H_2O_2$ synthesis), (E) standard conditions except $N_2$ is bubbled to remove $O_2$, and (F) standard conditions using Ti—$SiO_2$ material only, showing that it does not respond to the 365-nm UV light.

Figure 5:
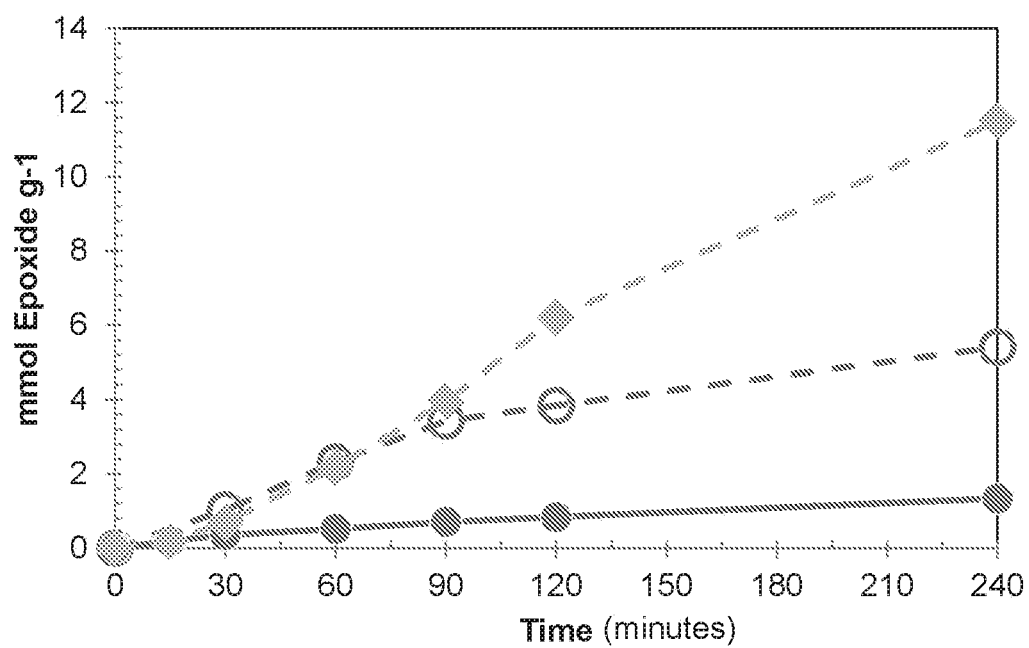

FIG. 5: Epoxide yields vs. time for the thermocatalytic epoxidation of cis-cyclooctene on Ti—$SiO_2$ for (●) 3.5 mmol $H_2O_2$ (50 wt %, aq.) added at once at the beginning of the reaction and (○) 0.2 mmol $H_2O_2$ (4.0 M dry in MeCN) added continuously at a rate of 0.1 mmol $h^{-1}$ over the course of the reaction, mimicking the in situ $H_2O_2$ production of the combined photo-/thermo-catalytic system. The yields for the combined photo-/thermo-catalytic system is also shown (✹).

Figure 6:
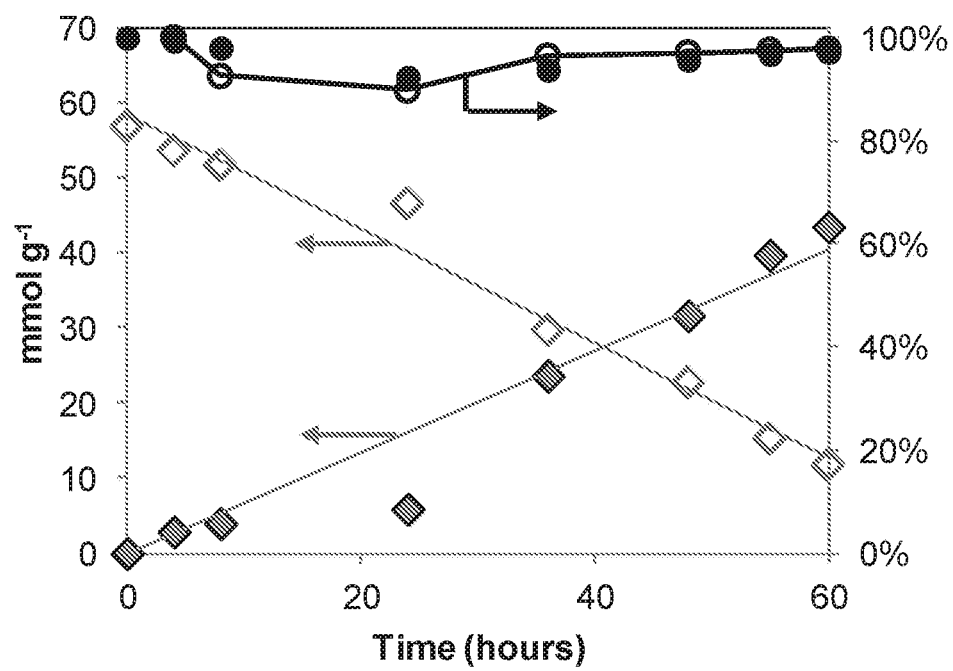

FIG. 6: Catalytic activity over an extended period of time, as shown through cis-cyclooctene (◇) and cyclooctene epoxide (◆) production, epoxide selectivity (○) and mass balance (●). Yields are reported per gram of photocatalyst.

Figure 7:
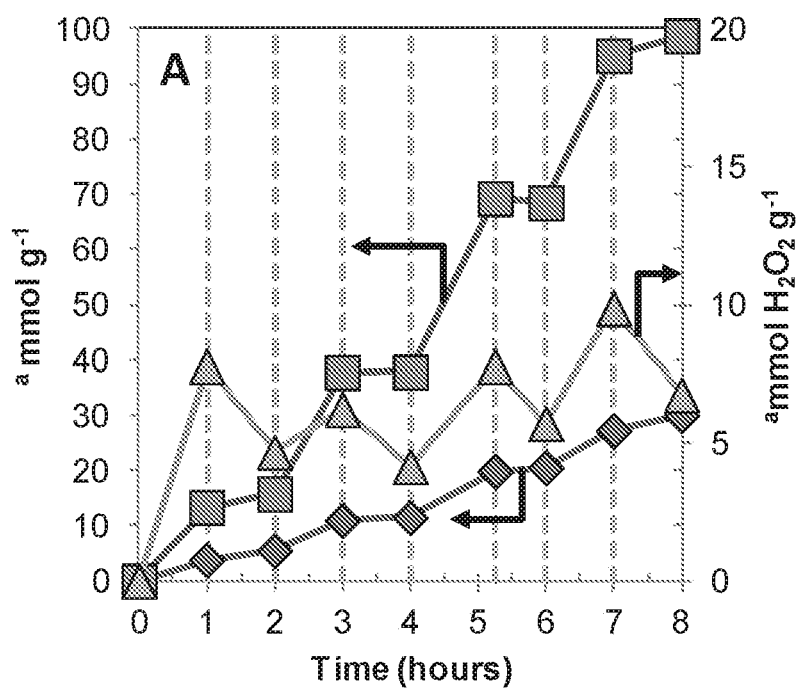

FIG. 7: UV light affect on reaction, as shown through Acetone (▨), cyclooctene epoxide (✹) and $H_2O_2$ (▨, right axis) production per gram of photocatalyst.

Figure 8:
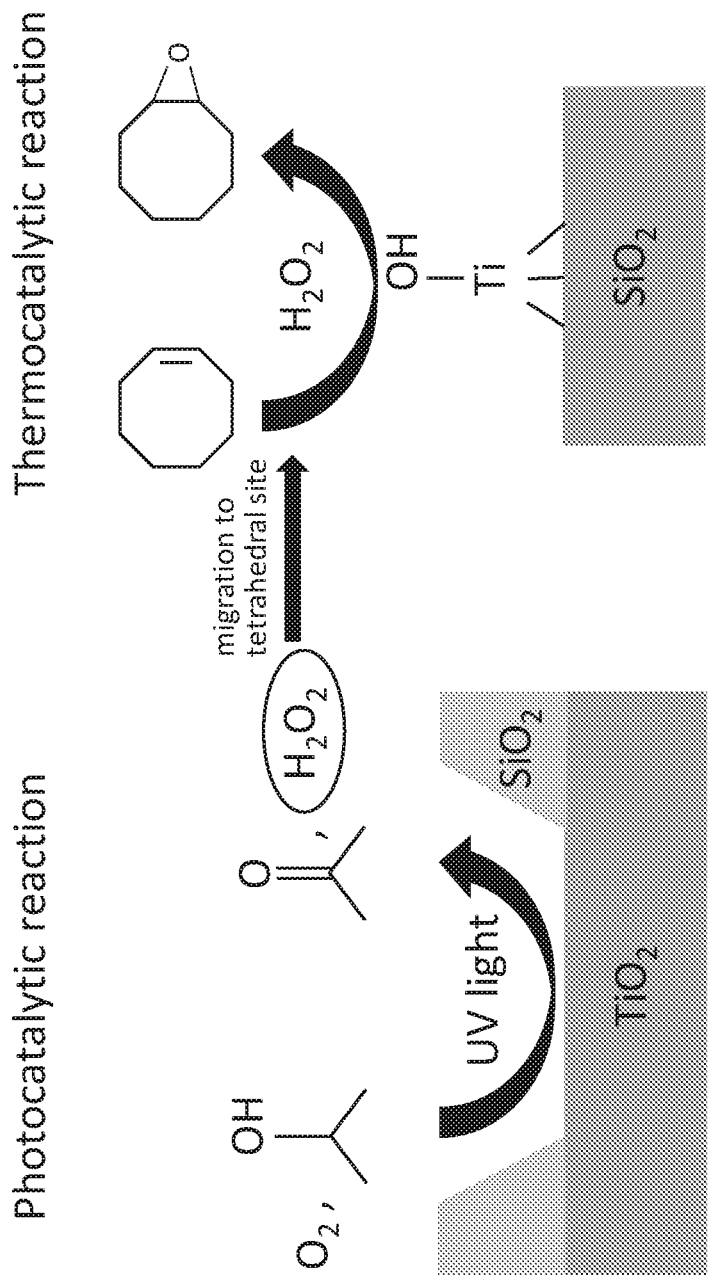

FIG. 8: Combined photo- and thermo-catalytic system for hydrogen peroxide production on $SiO_2$@$TiO_2$ (left) and subsequent consumption via alkene epoxidation on Ti—$SiO_2$ (right). Note that the Ti—$SiO_2$ site may exist on the surface of the $SiO_2$@$TiO_2$ material, as in Ti—$SiO_2$@$TiO_2$.

DETAILED DESCRIPTION OF CERTAIN EMBODIMENTS

As relates to one or more non-limiting embodiments of this invention, reference is made to FIG. 8. A $TiO_2$ surface is partially coated with silica (hereon referred to as $SiO_2$@$TiO_2$), and the resulting material is used to synthesize $H_2O_2$ photocatalytically from $O_2$ (in the air) and a proton donor/hole scavenger. In this case protons are generated and photo-generated holes are scavenged by the concurrent photocatalytic oxidation of isopropanol to acetone, but this can be achieved using many other sources, including other alcohols. If desired, the co-product acetone could be reduced with $H_2$ in a second step using existing art, thereby recycling the proton source and hole scavenger. The $H_2O_2$ generated in situ then migrates to an epoxidation site (e.g., either on the same or another catalyst particle) for use as an oxidant in alkene epoxidation—for instance, either, cis-cyclooctene to cyclooctane oxide or 1-octene to octane oxide. An example of such an epoxidation catalyst is Ti—$SiO_2$. Alternatively, the components necessary for performing these tasks can be combined onto a single catalyst particle by first overcoating a $TiO_2$ core with silica, then grafting dispersed Ti sites onto the silica (hereon referred to as Ti—$SiO_2$@$TiO_2$).

Performing $H_2O_2$ synthesis and epoxidation in such a combined photo/thermo system offers the following advantages over conventional $H_2O_2$ synthesis and epoxidation reactions: (i) $SiO_2$@$TiO_2$ is a more active photocatalyst than $TiO_2$ for $H_2O_2$ synthesis, (ii) the $H_2O_2$ does not need to be purified and concentrated, (iii) the $H_2O_2$ is not diluted with $H_2O$ (as is commercial $H_2O_2$), which is known to inhibit the epoxidation step, (iv) the epoxidation occurs at higher rates than the case where excess aqueous $H_2O_2$ is added at the start of the reaction.

Performance of the present invention is demonstrated through the following comparisons (Table 1, below, summarizes the catalytic performance of the materials):

$SiO_2$@$TiO_2$ gives higher yields of $H_2O_2$ at a given time than the $TiO_2$ core. Table 1 entry 1 gives the performance of the $TiO_2$ core material, while entry 2 gives the performance of $SiO_2$@$TiO_2$. $SiO_2$@$TiO_2$ yields 14 times greater $H_2O_2$ than the $TiO_2$ core alone. This is unexpected because the $SiO_2$ shell covers part of the active $TiO_2$ surface. The net $H_2O_2$ production on $SiO_2$@$TiO_2$ is equivalent to 21 mM $H_2O_2$ $h^{-1}$, which is 6 times greater than the best-performing previously reported photocatalysts for $H_2O_2$ synthesis (3.4 mM $H_2O_2$ $h^{-1}$). A TEM image of the $SiO_2$@$TiO_2$ catalyst is shown in FIG. 1, which shows that the catalyst comprises a $TiO_2$ core with a ~2 nm $SiO_2$ shell.

Addition of Ti—$SiO_2$ to a reactor with $SiO_2$@$TiO_2$ provides a catalyst system that can perform the thermocatalytic epoxidation reaction using in situ generated $H_2O_2$, as illustrated in FIG. 8. Entry 3 of Table 1 demonstrates that this physical mixture greatly increases the epoxide yield (compared to entries 1 & 2). Consequently, the $H_2O_2$ yield is reduced due to consumption of $H_2O_2$ by the epoxidation reaction. Producing the $H_2O_2$ in situ means that it does not need to be produced elsewhere, purified, concentrated, diluted, and finally transported to the reactor responsible for epoxidation. Instead, the $H_2O_2$ is not only produced on site, it is synthesized in the very same reactor as the epoxidation reaction.

The photo/thermo-catalytic system with in situ $H_2O_2$ production leads to higher rates of epoxidation when compared to conventional methods of epoxidation. Entry 4 of Table 1 displays the catalytic performance of Ti—$SiO_2$ for This system is not limited to Ti—$SiO_2$ as the epoxidation catalyst. Table 1, entries 8 and 9 display catalytic results for the combined photo-/thermo-catalytic system when using Ta—$SiO_2$ and Nb—$SiO_2$ as the thermocatalysts, respectively. As would be understood by those skilled in the art and made aware of this invention, most catalysts that use conventional $H_2O_2$ can also be utilized herewith.

TABLE 1

Product yields after 2 hours of reaction in photo-/thermo-catalytic system for various catalysts.

| Entry | Photocatalyst | Thermocatalyst | Acetone $^a$mmol g$^{-1}$ | $H_2O_2$ $^a$mmol g$^{-1}$ | Epoxide $^a$mmol g$^{-1}$ | $^b$mmol g$^{-1}$ |
|---|---|---|---|---|---|---|
| 1 | $TiO_2$ core | — | 42 | 3 | 0.4 | $^e$n/a |
| 2 | $SiO_2$@$TiO_2$ | — | 22 | 42 | 0.5 | $^e$n/a |
| 3 | $SiO_2$@$TiO_2$ | Ti—$SiO_2$ | 37 | 16 | 12 | 7 |
| $^c$4 | — | Ti—$SiO_2$ | $^d$n/a | $^d$n/a | $^d$n/a | 0.8 |
| $^f$5 | $SiO_2$@$TiO_2$ | Ti—$SiO_2$ | 42 | 9 | 3 | 2 |
| $^{c,f}$6 | — | Ti—$SiO_2$ | $^d$n/a | $^d$n/a | $^d$n/a | 0.1 |
| $^g$7 | Ti—$SiO_2$@$TiO_2$ | n/a | 14 | 13 | 3 | $^e$n/a |
| 8 | $SiO_2$@$TiO_2$ | Ta—$SiO_2$ | 48 | 25 | 14 | 3 |
| 9 | $SiO_2$@$TiO_2$ | Nb—$SiO_2$ | 32 | 6 | 8 | 6 |

Conditions: 5 mg photocatalyst (if present), 15 mg thermocatalyst (if present), 10 mL isopropanol, 1.15 mmol cis-cyclooctene, 65° C., 365 nm UV, $O_2$ bubbled every 30 minutes
$^a$Yield per gram of photocatalyst material.
$^b$Yield per gram of thermocatalyst material.
$^c$3.5 mmol $H_2O_2$ (aq) added.
$^d$Not applicable; no photocatalyst used.
$^e$Not applicable; no separate thermocatalyst used.
$^f$1-octene as alkene substrate g Ti—$SiO_2$@$TiO_2$ acting as thermocatalyst and photocatalyst a conventional thermocatalytic epoxidation reaction, when an excess of aqueous $H_2O_2$ is added at the beginning of the reaction and there is no photocatalytic cycle taking place to produce $H_2O_2$. The epoxide yield for the photo/thermo-catalytic system (entry 3) is 7 times greater than the conventional epoxidation system (entry 4). This is unexpected because the conventional system contains a much higher instantaneous concentration of $H_2O_2$ (3.5 mmol) than is measured in the combined photo/thermo-catalytic system (0.42 mmol, using the $H_2O_2$ yield from entry 2).

The photo/thermo-catalytic system with in situ $H_2O_2$ productions is active for other epoxidations. Table 1 entry 5 displays the catalytic performance for the combined system using 1-octene as the substrate. The rates of 1-octene epoxidation are 20 times higher for the combined photo/thermo-catalytic system than for a conventional thermocatalytic reaction (entry 6). 1-octene is a model reaction for the epoxidation of propylene, which is currently practiced at industrial scale over Ti—$SiO_2$ catalysts with added $H_2O_2$ by various industrial concerns.

The separate features of the $SiO_2$@$TiO_2$ photocatalyst and Ti—$SiO_2$ thermocatalyst can be combined onto a single catalyst particle to perform tandem photo- and thermo-catalytic functions. By grafting Ti onto the silica-overcoated $TiO_2$ core, a material capable of performing both catalytic reaction cycles can be obtained. Table 1 entry 7 displays the performance of single component catalyst Ti—$SiO_2$@$TiO_2$. While not achieving epoxide yields as high as the combined photo-/thermo-catalytic system (entry 3) this material still yields more epoxide than either $TiO_2$ or $SiO_2$@$TiO_2$, due to addition of tetrahedral Ti on the silica shell. The performance of this material may be improved by optimizing the $TiO_2$ morphology, the shell structure, or the Ti loading.

This system is not limited to Ti—$SiO_2$ as the epoxidation catalyst. Table 1, entries 8 and 9 display catalytic results for Table 2 summarizes physical characterization data from the materials examined. All of the $TiO_2$ based materials have edge energies of 3.2 eV, indicating that the addition of a silica shell does not change the photo-response of the $TiO_2$ core material. The edge energy of Ti—$SiO_2$ of 3.7 eV indicates that this material contains predominantly isolated Ti cations, with some clustered, non-tetrahedral Ti sites. Addition of the silica shell increases the surface area of the $TiO_2$ core, likely due to the formation of micropores, as indicated from the $N_2$ isotherm (FIG. 2). The crystal size does not significantly change with the addition of the silica shell. TEM images confirm the formation of a thin silica shell (FIG. 3). Taken together the characterization data show that the core-shell materials comprise a crystalline anatase $TiO_2$ core with a transparent ~2 nm microporous silica shell.

TABLE 2

Physical characterization data of materials

| Material | $E_g{}^a$ eV | Surface Area$^b$ m$^2$ g$^{-1}$ | Crystallite size$^c$ nm |
|---|---|---|---|
| $TiO_2$ core | 3.2 | 43 | 23 |
| core-shell | 3.2 | 57 | 27 |
| Ti-core-shell | 3.2 | 56 | 27 |
| Ti-$SiO_2$ | 3.7 | 589 | — |

$^a$Estimated from DRUV-visible spectra transformed with a tauc plot.
$^b$Estimated from $N_2$ physisorption using the BET method.
$^c$Estimated from XRD; only anatase $TiO_2$ is observed As illustrated by Table 1 entries 1-3, addition of the silica shell unexpectedly enhances $H_2O_2$ production, while addition of Ti to the shell surface increases the epoxidation activity. To prove that the reaction proceeds as illustrated in FIG. 8, several control reactions were performed with the combination Ti—$SiO_2$@$TiO_2$ catalyst (FIG. 4). Removing any component of the combined photo-/thermo-catalytic system reduces or eliminates production of epoxide, confirming that the reaction proceeds through the photocatalytic production of hydrogen peroxide from isopropanol and the subsequent epoxidation of cis-cyclooctene via hydrogen peroxide. Comparing the combined photo/thermocatalytic systems for both alkenes (entries 3 and 5 from Table 1) to conventional thermocatalytic reactions (entries 4 and 6 from Table 1) shows that epoxidation rates for the combined system are unexpectedly 7 times greater for cis-cyclooctene and 20 times greater for 1-octene. Finally, FIG. 5 shows that slowly adding dry $H_2O_2$ over the course of the reaction increases epoxide yields vs. the case where $H_2O_2$ is added all at once, but still does not reach the productivity of the combined photo-/thermo-catalytic system. Thus, without limitation to any one theory or mode of operation, a combined photo-/thermo-catalytic system may improve epoxide yields by slowly synthesizing $H_2O_2$ in parallel with its consumption. Further, and also without limitation, comparing yields of $H_2O_2$ and acetone, the $SiO_2$@$TiO_2$ material may be improving $H_2O_2$ yields by inhibiting the unproductive, subsequent decomposition of $H_2O_2$, as opposed to accelerating the production of $H_2O_2$.

Accordingly, the present invention describes catalytic materials and method(s) for the photocatalytic production of $H_2O_2$ in the same reactor as the subsequent consumption of $H_2O_2$ in a useful chemical transformation (e.g., alkene epoxidation). Such methods avoid $H_2O_2$ purification and transport, and greatly simplify the total production process. A representative photocatalyst described herein for $H_2O_2$ synthesis exhibits significantly higher synthesis rates than those previously reported, and the epoxidation rates for a combined system are higher than those observed for a conventional system, due to the intimate coupling of $H_2O_2$ generation and consumption.

EXAMPLES OF THE INVENTION

The following non-limiting examples and data illustrate various aspects and features relating to the catalyst materials and/or methods of the present invention, including unitary photo- and thermocatalytic nanoparticles, as are available through the synthetic methodologies described herein. In comparison with the prior art, the present methods and catalyst materials provide results and data, which are surprising, unexpected and contrary thereto. While the utility of this invention is illustrated through the use of several catalyst materials, proton donor and reactant components which can be used therewith, it will be understood by those skilled in the art that comparable results are obtainable with various other catalyst materials, proton donor and reactant components, as are commensurate with the scope of this invention.

Example 1

Synthesis of $SiO_2$@$TiO_2$ core-shell. Anatase $TiO_2$ nanoparticles were used as received from Sigma-Aldrich (<25 nm particles, "$TiO_2$ core"). 2 g of the $TiO_2$ core, 50 mL ethanol (KOPTEC, 200 proof), 3.2 mL NH4OH solution (56.6 w/w %) were added to a plastic container, sonicated for 30 minutes to disperse the oxide particles and equilibrate the pH. The mixture was transferred to a shaker plate, shaking at 200-250 rpm, and 1 mL of tetraethoxyorthosilicate (TEOS, Sigma-Aldrich) was added in 0.1 mL increments every 20 minutes while shaking the vial in between. The mixture was allowed to shake overnight then centrifuged to collect solids. The solids were resuspended in 50 mL of 18 MΩ deionized water then centrifuged to wash away excess TEOS and $NH_4OH$. This washing step was repeated 5 times. Finally the solids were collected and dried in a drying oven at 150° C. for 12 to 15 hours.

Various other methods for $SiO_2$@$TiO_2$ synthesis can be utilized, including the use of other core materials, $SiO_2$ precursors, and deposition conditions, as would be understood by those skilled in the art.

Example 2

Synthesis of Ti—$SiO_2$@$TiO_2$. The core-shell material of Example 1 was dried under vacuum (<200 mTorr) at 200° C. for 12 to 15 hours to remove physisorbed water. In a separate round-bottomed flask titanocene dichloride ($C_{10}H_{10}Cl_2Ti$, Aldrich 97%) was dissolved in freshly-distilled anhydrous toluene. In an Ar-filled glovebox the dried core-shell support was added to the round-bottomed flask and sealed. The round-bottomed flask was then removed from the glovebox and attached to a condenser and refluxed under $N_2$ for 48 hours. The reflux occurred without stirring to avoid grinding the core-shell particles. The material was then collected via vacuum filtration where it was washed with 200 mL toluene, 400 mL acetonitrile, and allowed to dry at room temperature overnight.

Various other methods of adding Ti to $SiO_2$@$TiO_2$ can be utilized, including the use of other precursors and deposition methods as would be understood by those skilled in the art. Likewise, as would be understood in the art, other catalytically active cations can be coupled to the $SiO_2$ surface, such as thermocatalytic transition metals of the sort described elsewhere herein, through use of, for instance, corresponding metallocene starting materials.

Example 3

Synthesis of Ti—$SiO_2$. Mesoporous silica ($SiO_2$, Selecto, 540 $m^2$ $g^{-1}$, 2.2 nm average pore radius, 100-200 µm particles) was dried under vacuum (<200 mTorr) at 500° C. for 12 to 15 hours and stored under $N_2$ before use. 4-tert-butyldimethoxycalix[4]-arene ($C_{46}H_{60}O_4$, "$CxMe_2$") was synthesized by methylating 4-tert-butylcalix[4]arene ($C_{44}H_{56}O_4$, "Cx", Sigma-Aldrich) with methyl iodide, following a literature procedure. Titanium-tert-butyl-calix[4]-arene chloride (TiCx) was synthesized by adding $TiCl_4$ (1.0 M in tolene, Sigma-Aldrich) to a solution of $CxMe_2$ in toluene and refluxed for 48 hours. The dried silica was then added to the TiCx solution in an Ar-filled glovebox, then removed from the glovebox and refluxed in toluene for >72 hours. During reflux $N_2$ was continuously bubbled through the reaction solution and vented through the top of the condenser to remove HCl. The TiCx-$SiO_2$ material was collected via vacuum filtration and repeatedly washed with toluene until the filtrate was clear (approximately 400 mL per g of material). The material was washed further with THF then water and dried at room temperature under vacuum. The final titanium loading was 200 µmol $g^{-1}$ or 1 wt % Ti, as determined by ICP-AES.

Example 4

Synthesis of Ta—$SiO_2$. Mesoporous silica ($SiO_2$, Selecto, 540 $m^2$ $g^{-1}$, 2.2 nm average pore radius, 100-200 µm particles) was dried under vacuum (<200 mTorr) at 500° C. for 12 to 15 hours and stored under $N_2$ before use. To obtain tantalum-tert-butyl-calix[4]-arene (TaCx), $TaCl_5$ was refluxed in toluene with 1 equivalent of Cx to form TaCx. The dried silica was then added to the TaCx solution in an Ar-filled glovebox, then removed from the glovebox and refluxed in toluene for >72 hours. During reflux $N_2$ was continuously bubbled through the reaction solution and vented through the top of the condenser to remove HCl. The TaCx-SiO$_2$ material was collected via vacuum filtration and repeatedly washed with toluene until the filtrate was clear (approximately 400 mL per g of material). The material was washed further with THF then water and dried at room temperature under vacuum.

Example 5

Synthesis of Nb—SiO$_2$. Mesoporous silica (SiO$_2$, Selecto, 540 m$^2$ g$^{-1}$, 2.2 nm average pore radius, 100-200 μm particles) was dried under vacuum (<200 mTorr) at 500° C. for 12 to 15 hours and stored under N$_2$ before use. To obtain niobium-tert-butyl-calix[4]-arene (NbCx), NbCl$_5$ was refluxed in toluene with 1 equivalent of Cx to form NbCx. The dried silica was then added to the NbCx solution in an Ar-filled glovebox, then removed from the glovebox and refluxed in toluene for >72 hours. During reflux N$_2$ was continuously bubbled through the reaction solution and vented through the top of the condenser to remove HCl. The NbCx-SiO$_2$ material was collected via vacuum filtration and repeatedly washed with toluene until the filtrate was clear (approximately 400 mL per g of material). The material was washed further with THF then water and dried at room temperature under vacuum.

As indicated above, various other thermocatalysts can be utilized, including most transition metal cations supported on SiO$_2$, and many other materials useful in catalytic oxidation with H$_2$O$_2$.

Example 6

Catalytic reactions. Prior to all catalytic reactions, the materials described above were calcined at 600° C. for 2 hours in static air. For the combined photo-/thermo-catalytic reaction system 5 to 10 mg of photocatalyst (TiO$_2$ core, SiO$_2$@TiO$_2$ or Ti—SiO$_2$@TiO$_2$) and 0 to 70 mg of thermocatalyst (Ti—SiO$_2$, Ta—SiO$_2$ or Nb—SiO$_2$) were added to a 20 mL reaction vial with 10 mL isopropanol, 1.15 mmol alkene (cis-cyclooctene or 1-octene) and 150 uL dodecane as an internal standard. A hole was punched into the reaction vial septum to allow the fitting of a quartz test tube to hold the 365 nm pen-ray UV lamp. Prior to reaction the reaction mixture was sonicated for 5 minutes to disperse any aggregated particle and then allowed to heat up to 65° C. for 30 minutes. The UV lamp was allowed to warm-up for 30 minutes prior to starting the reaction. O$_2$ was bubbled through the reaction solution for 5 minutes prior to starting the reaction, and then for 1 minute at each sampling interval (0, 30, 60, 90, 120 minutes).

The reaction was started by introducing the pen-ray lamp to the reaction mixture and the vessel was agitated using a Glas-Col shaker plate. 150 μL aliquots were collected into GC vials with ~1 mg Ag powder to decompose any H$_2$O$_2$ and avoid overoxidation. Acetone, cis-cyclooctene and cyclooctene oxide were quantified by GC-FID. H$_2$O$_2$ was quantified by iodometry (see below). For thermal reactions, 10 to 30 mg of thermocatalyst were added to a 20 mL reaction vial with 10 mL isopropanol, 1.15 mmol alkene, 150 uL dodecane as internal standard, sonicated for 5 minutes, allowed to heat up to 65° C. for 30 minutes, and then 3.5 mmol H$_2$O$_2$ (either from aqueous 50 wt % H$_2$O$_2$ or 4.0 M H$_2$O$_2$ in MeCN dried via MgSO$_4$) is added to initiate the reaction. Alternatively, in one control reaction H$_2$O$_2$ (dried, in MeCN) is added at a rate of 100 μmol h$^{-1}$ continuously over the course of the reaction with a syringe pump.

Example 7

Catalyst activity can be demonstrated through extended reaction. A physical mixture of SiO$_2$@TiO$_2$ photocatalyst and Ti—SiO$_2$ thermocatalyst was run with 60 mM cyclooctene in isopropanol. With reference to FIG. 6, conversion of alkene reaches 79% after 60 hours with 98% selectivity towards cyclooctene epoxide (97% mass balance, shown in black, where mass balance is ([Alkene]$_t$+[Epoxide]$_t$)/[Alkene]$_{initial}$). O$_2$ is bubbled through periodically.

Example 8

Reaction can be affected via the illumination source. With reference to Example 1, reaction conditions were as follows: 5 mg SiO$_2$@TiO$_2$, 15 mg Ti—SiO$_2$, 10 mL isopropanol, 1.15 mmol cis-cyclooctene, 65° C., 365 nm UV (between 0-1, 2-3, 4-5 hours, etc.); O$_2$ bubbled every 30 minutes. As shown in FIG. 7, periods of illumination produce hydrogen peroxide and acetone. Hydrogen peroxide is consumed during dark periods, while no acetone is produced. As long as sufficient hydrogen peroxide is present, cyclooctene epoxide formation continues during light and dark cycles.

Example 9

In accordance with certain embodiments of this invention, hydrogenation can be used to regenerate a starting alcohol proton donor, as shown in Scheme 1.

Scheme 1.

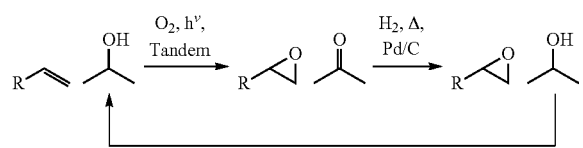

Acetone hydrogenation was performed to demonstrate the recovery of isopropanol from the photocatalytic oxidation system. A reaction solution was prepared with 1.1 mmol acetone, 0.4 mmol cyclooctene oxide, and dodecane as internal standard in 50 mL isopropanol. Prior to hydrogenation, Pt on activated carbon ("Pt/C", 1 wt % Pt, Aldrich) was heat treated to 400° C. for 4 hours under flowing He, ~1 mL min in a u-tube reactor. The Pt/C catalyst was sealed within the u-tube until use for hydrogenation. The reaction solution and 230 mg of Pt/C was loaded and sealed into a high-pressure Parr reactor, de-gassed with N$_2$, then charged with 10 bar H$_2$. Hydrogenation occurred at 10 bar H$_2$, 50° C., with stirring at 600 rpm. After 18 hours the reactor was cooled, de-pressurized, and an aliquot was collected for GC analysis: no epoxide was consumed under these conditions, whereas 100% of the acetone was hydrogenated.

Example 10

Iodometric titration of H$_2$O$_2$. H$_2$O$_2$ was quantified by iodometry adapting previously described literature techniques. After 2 hours of reaction 200 µL aliquots were added to 1 mL of 50 v/v % $H_2SO_4$ and $N_2$ was bubbled through the solution for 10 minutes to remove $O_2$. Then 1 w/w % KI (aq) was added to form $I_2$, which was a yellow solution. The solution was titrated with 0.1 mM $Na_2S_2O_3$ until the solution color was faintly yellow, then 0.1 mL starch indicator was added, forming a dark purple color, and the solution was further titrated until colorless. The $Na_2S_2O_3$ titrant was standardized with solutions of $KI_3$.

Example 11

Characterization. All catalyst samples were calcined for 2 hours at 600° C. prior to characterization.

TEM images were obtained using a JEOL 2100F transmission electron microscope. Catalyst samples were suspended in methanol, sonicated for 5 minutes, then platinum TEM grids were dipped into the suspension and dried at room temperature before imaging.

Diffuse-reflectance UV-visible spectra were collected with a UV-3600 Shimadzu spectrophotometer with a Harrick Praying Mantis accessory for powder measurements and polytetrafuoroethylene as the baseline reference. Reflectance spectra were converted with the Kebulka-Munk transformation and edge energies were taken from Tauc plots of the spectra.

$N_2$ physisorption measurements were performed on a Micromeritics ASAP 2010. Prior to analysis, powder samples were dried at 200° C. under vacuum (<5 µm Hg). Surface areas were calculated by the BET method.

X-ray diffraction (XRD) spectra were collected with a Rigaku X-ray diffractometer from 20 to 60° 2θ, with Cu Kα radiation. The slit width, dwell time and slit widths were kept constant for all materials. Crystallite sizes were estimated using the Scherrer equation for the (101) anatase reflection at a Bragg angle of 25.2° 2θ, assuming a shape factor of 0.9 with a lower detection limit of approximately 5 nm.

$H_2O_2$ is widely used as a "green" oxidant for chemical synthesis, because it is efficient, selective, and has only water as a byproduct. In situ $H_2O_2$ generation for selective oxidation has long been a goal of catalysis, specifically so for propylene epoxidation. As demonstrated, above, this invention provides an excellent catalyst for $H_2O_2$ production from $O_2$ and a proton donor. In addition, $H_2O_2$ production can be coupled to a thermocatalyst for epoxidation, thus preventing the need to purify, concentrate, then dilute $H_2O_2$ for sale and transport. This invention also demonstrates oxidation of 1-octene, a model substrate for epoxidation of linear alkenes, indicating to those skilled in the art, broader applicability to other synthetic processes, including the production of propylene oxidation.

We claim:

1. A method for concomitant $H_2O_2$ production and reaction using a catalyst composition comprising:
   a particulate $TiO_2$ core component, the particulate $TiO_2$ core component having a surface;
   a $SiO_2$ shell component coupled to and partially coating the surface of the particulate $TiO_2$ core component; and
   transition metal moieties coupled to the $SiO_2$ shell component, wherein $TiO_2$ surface areas of the particulate $TiO_2$ core component are exposed through the $SiO_2$ shell component, the method comprising:
   exposing the catalyst composition to a reaction medium comprising $O_2$, a proton donor, and an alkene; and
   irradiating the reaction medium with ultra-violet light to induce the photocatalytic oxidation of the proton donor and the formation of $H_2O_2$, whereby the $H_2O_2$ and the alkene undergo an oxidation reaction to form an oxidation product, wherein the oxidation of the proton donor and the oxidation reaction are both catalyzed by the catalyst composition.

2. The method of claim 1, wherein the proton donor is an alcohol.

3. The method of claim 1, wherein the proton donor is a linear alkene.

4. The method of claim 1, wherein the transition metal moieties comprise V, Ti, Cr, Mn, Co, Cu, Zn, Mo, Nb, Ta, W, Os, Re, Ir, Sn, or a combination thereof.

5. The method of claim 1, wherein the transition metal moieties comprise Ti.

6. The method of claim 5, wherein the alkene is propylene, and the oxidation product is propylene oxide.

7. The method of claim 2, wherein the alcohol is isopropanol.

8. The method of claim 7, wherein the photocatalytic oxidation of the isopropanol produces acetone.

9. The method of claim 8, further comprising hydrogenating the acetone to regenerate the isopropanol.

10. The method of claim 1, wherein the oxidation reaction is an epoxidation reaction.

11. The method of claim 10, wherein the alkene is a cycloalkene.

12. The method of claim 11, wherein the cycloalkene is cyclooctene.

13. The method of claim 11, wherein the proton donor is an alcohol.

14. The method of claim 1, wherein the irradiation is intermittent.

* * * * *